United States Patent [19]
Hök et al.

[11] 4,413,528
[45] Nov. 8, 1983

[54] MINIATURE PRESSURE TRANSDUCER

[75] Inventors: Bertil Hök, Västeras; Gösta Säll, Norsborg, both of Sweden

[73] Assignee: Siemens Aktiengesellschaft, Berlin & Munich, Fed. Rep. of Germany

[21] Appl. No.: 254,408

[22] Filed: Apr. 15, 1981

[30] Foreign Application Priority Data

May 21, 1980 [DE] Fed. Rep. of Germany ....... 3019464

[51] Int. Cl.³ .............................................. G01L 9/02
[52] U.S. Cl. ..................................... 73/753; 128/673; 128/675; 338/38
[58] Field of Search ............... 137/455, 458, 505, 848, 137/188, 217, 218; 128/748, 678, 675; 73/753; 338/36, 38, 42

[56] References Cited

U.S. PATENT DOCUMENTS

| | | | |
|---|---|---|---|
| 2,629,399 | 2/1953 | Kulick | 137/525 |
| 3,239,101 | 3/1966 | Wilson | 222/52 |
| 3,566,875 | 3/1971 | Stoehr | 128/350 |
| 4,261,208 | 4/1981 | Hök et al. | 73/753 |
| 4,297,890 | 11/1981 | Hök | 73/753 |

OTHER PUBLICATIONS eds. Fleming, D. G.; Ko, W. H.; Neuman, M. R.; *Indwelling and Implantable Pressure Transducers*; 1977; CRC Press; pp. 3-34; 1975.

*Primary Examiner*—B. A. Reynolds
*Assistant Examiner*—M. M. Lateef
*Attorney, Agent, or Firm*—Hill, Van Santen, Steadman & Simpson

[57] ABSTRACT

In an exemplary embodiment, an electrical signal is to be generated corresponding to the pressure to be measured. The pressure transducer is formed by an outer tube in which a measuring cell as well as a liquid line connected to a liquid reservoir are disposed. In order to be able to calibrate the pressure transducer at the respective place of measurement, for example, a blood vessel, the disclosure provides that the open end of the outer tube is closed by a one-way valve through which fluid can only flow out in the direction from the tube. When a slight, specific underpressure is set, the one-way valve closes and the pressure transducer can be calibrated.

5 Claims, 3 Drawing Figures

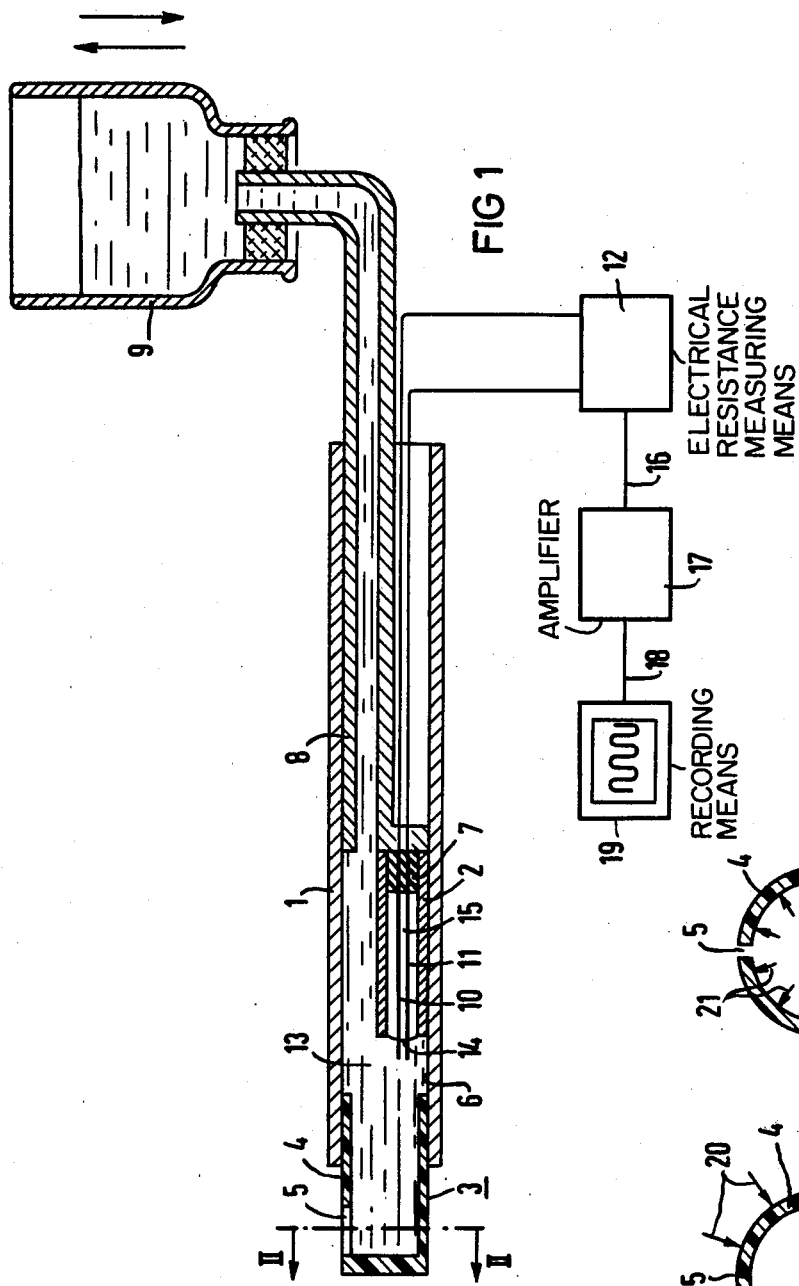

MINIATURE PRESSURE TRANSDUCER

BACKGROUND OF THE INVENTION

The invention relates to a miniature pressure transducer for generating an electrical signal which corresponds to a hydrostatic pressure to be measured in a liquid vessel, comprising a measuring cell disposed in an outer tube, said measuring cell having means for generating an electrical magnitude corresponding to the pressure to be measured, as well as comprising a fluid line for the passage of fluid into a chamber which is formed, on the one hand, by the mouth of the fluid line and/or by the measuring cell and, on the other hand, by the inside wall of the outer tube and which can be directly connected via an opening to the fluid in the liquid vessel.

A miniature pressure transducer of this type is known from the German OS 28 11 859. This pressure transducer, which is provided for physiological pressure measurements, exhibits a tube opening at its end face which lies frontally opposite the opening of the measuring cell. Before the pressure transducer is introduced into the liquid vessel, it must first be filled with liquid and then be calibrated. A possible disadvantage of calibrating at this point in time is that the output signal of the pressure transducer can change until it is situated at the location to be measured in the liquid vessel. This disadvantage of the pressure transducer can be partially avoided in that it is removed from the vessel at periodic intervals and is re-calibrated. This, however, is involved and an annoyance for the patient.

SUMMARY OF THE INVENTION

The object of the invention is to create a pressure transducer of the type initially cited in which calibration can be undertaken at any time directly in the liquid vessel. A further object of the invention resides in preventing a contamination of the measuring cell with the liquid from the liquid vessel.

This object is inventively achieved in that a one-way valve is disposed in the opening of the chamber, given which the liquid can only flow in the direction from the chamber into the liquid vessel.

Due to the one-way valve, the pressure transducer can now be directly calibrated in the liquid vessel. To that end, a liquid reservoir connected to the liquid line is placed at a specific height with respect to the pressure transducer. By placing the liquid reservoir at a specific height with respect to the pressure transducer, a specific, reproducible pressure is produced in the chamber. With this specific, reproducible pressure produced in the chamber, the one-way valve is closed.

Further advantages and details of the invention derive from the subclaims.

In the following, the invention is described in greater detail on the basis of an exemplary embodiment illustrated on the accompanying drawing sheet; and other objects, features and advantages will be apparent from this detailed disclosure and from the appended claims.

BRIEF DESCRIPTION OF THE DRAWINGS

FIG. 1 is a longitudinal section through an inventive pressure transducer for the purpose of measuring blood pressure; and FIGS. 2 and 3 are cross-sections through the pressure transducer according to FIG. 1 taken along the line II—II.

DETAILED DESCRIPTION

FIG. 1 shows that the miniature pressure transducer exhibits an outer tube 1 as well as an inner tube 2 which forms the measuring cell and is surrounded by said outer tube. A one-way valve 3 is secured at the free end of the outer tube 1. The one-way valve 3 consists of a single piece with a sealing and with a spring-back part. The spring-back part 4 is designed as a cylinder whose free end facing away from the outer tube is closed. The one-way valve 3 is further provided with a slot 5 which is disposed in the longitudinal direction of the cylinder 4 and which serves as a sealing member. The one-way valve can be made of a synthetic material, for example, silicon rubber. The measuring cell 2 is disposed in the outer tube 1 and is secured to its inner wall 6. The measuring cell 2 is closed at its end 7 facing away from the one-way valve 3 of the pressure transducer. Moreover, the measuring cell 2 ends at a distance from the free end of the outer tube 1. A gap for a liquid line 8 is left free between the outer tube 1 and the measuring cell 2, said liquid line being connected to a liquid reservoir 9 with a salt solution. The mouth of the liquid line 8 and the measuring cell 2, on the one hand, and the inside wall 6 of the outer tube and the one-way valve 3, on the other hand, form a chamber 13. A salt solution which is under a specific pressure is contained in the liquid reservoir 9. The flow resistance which, among other things, is determined by the diameter of the liquid line 8 is dimensioned in such manner that it is significantly lower than the leakage resistance of the one-way valve 3 in its closed state and is significantly greater than the flow resistance of the one-way valve 3 in its opened state.

Two electrodes 10 and 11 consisting of platinum are arranged at an interval in the measuring cell 2 and extend in the longitudinal direction of the tube, said electrodes projecting from the open end of the measuring cell 2 and being connected to a device 12 for measuring the respective resistance between them.

When blood pressure is to be measured, the pressure transducer must be filled with salt solution before it is introduced into the measuring location, for example into a blood vessel. To that end, salt solution flows from the liquid reservoir 9 via the liquid line 8 into the chamber 13 and expresses the air in the pressure transducer through the slot 5 into the atmosphere. Due to the small dimensions of the pressure transducer, the salt solution flows into the chamber and fills it independently of the pressure of the liquid reservoir. A meniscus 14 is formed in the area of the free end of the measuring cell 2. Due to the electrodes 10 and 11 which have been elongated in comparison to the pressure transducer known from the German OS 28 11 859, it is no longer necessary to displace said meniscus into the measuring cell in that air is removed from it.

For measuring blood pressure, the pressure transducer is now introduced into a blood vessel of a patient, whereby the gas volume 15 enclosed in the measuring cell 2 changes. The respective gas volume corresponds to the pressure of the salt solution and, thus, to the pressure to be measured and, as described in the German OS 28 11 859, is converted into an electrical signal in the device 12. The device 12 is in turn connected via the connection 16 to an amplifier 17 for amplifying the signals from the device 12. The amplifier 17 is in turn connected via the connection 18 to a recording means 19 for recording the measured results.

The pressure transducer can now be calibrated directly in the blood vessel before and/or between measurements. This ensues in that the liquid reservoir 9 is placed at a specific height with respect to the pressure transducer. By so doing, a specific pressure is set in the chamber 13 of the pressure transducer at which the slot 5 of the one-way valve 3 is closed. The calibration can be undertaken. After calibration, the liquid reservoir 9 is moved in such manner that the liquid in the chamber 13 exhibits a somewhat higher pressure than in the blood vessel, so that the slot 5 is opened due to the pressure in the chamber 13 and salt solution seeps out of it, whereby a pressure measurement can be undertaken.

FIG. 2 shows the slot 5 in its closed state. The arrows 20 in this figure show that an underpressure exists in the chamber 13 in comparison to its environment.

FIG. 3 shows the slot 5 in its open state. Here, the arrows 21 show that an excess pressure prevails in the chamber in comparison to its environment.

The wall thickness of the cylinder 4 and the elasticity of the wall determine the back-spring of the one-way valve 3.

In the manner just described, the pressure transducer can be calibrated at any time when a measurement is undertaken in a blood vessel without having to withdraw it from the blood vessel.

The dimensions of the pressure transducer can be kept very small. In the exemplary embodiment, the outer diameter of the outer tube amounted to 0.8 mm and the length of the chamber 13 including the one-way valve amounted to 5 mm. The slot of the one-way valve had a length of 0.5 mm.

It will be apparent that many modifications and variations may be effected without departing from the scope of the novel concepts and teachings of the present invention.

We claim as our invention:

1. A miniature pressure transducer for generating an electrical signal which corresponds to a hydrostatic pressure to be measured in a liquid vessel, comprising an outer tube, a measuring cell disposed in the outer tube, said measuring cell having means for generating an electrical magnitude corresponding to the pressure to be measured, fluid chamber defining means comprising said outer tube defining a chamber in fluid communication with said measuring cell so that the pressure of said chamber is sensed by said measuring cell, a liquid line for the passage of liquid into the chamber, and fluid coupling means for coupling the chamber to liquid whose pressure is to be measured, in a liquid vessel external to said outer tube, wherein the improvement comprises said fluid coupling means being a one-way valve (3) disposed between the chamber (13) and the exterior of said outer tube such that the liquid can only flow in the direction from the chamber (13) into the liquid vessel, said one-way valve (3) consisting of one piece with a sealing and with a spring-back part (4, 5) consisting of a flexible material.

2. A miniature pressure transducer according to claim 1, characterized in that the sealing and the spring-back part (4, 5) consist of silicon rubber.

3. A miniature pressure transducer according to claim 1, with the spring-back part (4) being designed as a cylinder closed at the outward-facing end of the chamber (13) and in that the sealing part consists of a slot (5) in said cylinder.

4. A miniature pressure transducer according to claim 3, characterized in that the slot (5) is disposed in the longitudinal direction of the cylinder (4).

5. A miniature pressure transducer according to claim 1, with the liquid line (8) being dimensioned in such manner that its flow resistance is significantly lower than the leakage resistance of the one-way valve (3) in its closed state and significantly greater than the flow resistance of the one-way valve (3) in its open state.

* * * * *